(12) United States Patent
Boyer et al.

(10) Patent No.: US 10,799,254 B2
(45) Date of Patent: **\*Oct. 13, 2020**

(54) ARTIFICIAL PROSTHESIS INSTALLATION CLAMP AND METHOD

(71) Applicant: Boyer Anderson, LLC, Henrico, VA (US)

(72) Inventors: John Stuart Boyer, Henrico, VA (US); Bruce Reed Anderson, Richmond, VA (US)

(73) Assignee: Boyer Anderson, LLC, Henrico, VA (US)

( * ) Notice: Subject to any disclaimer, the term of this patent is extended or adjusted under 35 U.S.C. 154(b) by 119 days.

This patent is subject to a terminal disclaimer.

(21) Appl. No.: 16/048,589

(22) Filed: Jul. 30, 2018

(65) Prior Publication Data
US 2019/0125372 A1    May 2, 2019

Related U.S. Application Data

(63) Continuation of application No. 15/798,472, filed on Oct. 31, 2017, now Pat. No. 10,034,679.

(51) Int. Cl.
*A61B 17/17* (2006.01)
*A61F 2/46* (2006.01)
(Continued)

(52) U.S. Cl.
CPC ...... *A61B 17/1767* (2013.01); *A61B 17/8802* (2013.01); *A61B 17/885* (2013.01); *A61B 17/8866* (2013.01); *A61B 17/8872* (2013.01); *A61F 2/461* (2013.01); *A61B 2017/00128* (2013.01); *A61B 2017/00407* (2013.01); *A61B 2017/00526* (2013.01); *A61B 2090/064* (2016.02); *A61B 2090/0813* (2016.02); *A61F 2/3877* (2013.01); *A61F 2002/30507* (2013.01); *A61F 2002/4622* (2013.01); *A61F 2002/4628* (2013.01); *A61F 2002/4631* (2013.01); *A61F 2002/4666* (2013.01)

(58) Field of Classification Search
CPC .............................. A61B 17/1767; B25B 5/10
See application file for complete search history.

(56) References Cited

U.S. PATENT DOCUMENTS 5,342,364 A * 8/1994 Mikhail ............. A61B 17/2812
606/79
5,575,793 A * 11/1996 Carls ................. A61B 17/1735
606/80

(Continued)

*Primary Examiner* — Andrew Yang
(74) *Attorney, Agent, or Firm* — Williams Mullen; Thomas F. Bergert

(57) ABSTRACT

In the use of devices and methods for measuring applied pressure on an article, such as a patella construct during a surgical procedure, a clamp is provided with arms, an optional external spring, an optional internal spring and a torque knob for applying constant and measurable pressure to the article. Embodiments of the clamp include a spring rod engaged with the torque knob for assisting in applying and retaining desired pressure. Spike elements and a bushing insert are secured to the ends of the arms for retaining the article in place during use. The elements are advantageously assembled and disassembled to facilitate thorough and quick cleaning.

10 Claims, 5 Drawing Sheets

(51) Int. Cl.
*A61B 17/88* (2006.01)
*A61F 2/38* (2006.01)
*A61B 90/00* (2016.01)
*A61B 17/00* (2006.01)
*A61F 2/30* (2006.01)

(56) References Cited

U.S. PATENT DOCUMENTS

| | | | | |
|---|---|---|---|---|
| 5,716,360 | A * | 2/1998 | Baldwin | A61B 17/1677 606/79 |
| 5,885,298 | A * | 3/1999 | Herrington | A61B 17/1767 606/88 |
| 5,941,884 | A * | 8/1999 | Corvelli | A61B 17/1677 606/102 |
| 6,159,246 | A * | 12/2000 | Mendes | A61B 17/1767 606/80 |
| 6,866,667 | B2 * | 3/2005 | Wood | A61B 17/1767 606/86 R |
| 8,951,262 | B2 * | 2/2015 | Kecman | A61B 17/1767 606/96 |
| 9,131,974 | B1 * | 9/2015 | Boyer | A61B 17/1767 |
| 9,402,746 | B2 * | 8/2016 | Boyer | A61F 2/4657 |
| 9,554,813 | B2 * | 1/2017 | Clever | A61B 17/1767 |
| 2013/0165939 | A1 * | 6/2013 | Ries | A61B 17/8863 606/88 |
| 2013/0211410 | A1 * | 8/2013 | Landes | A61B 17/158 606/88 |
| 2016/0278794 | A1 * | 9/2016 | Boldt | A61F 2/3877 |
| 2017/0281202 | A1 * | 10/2017 | Hampp | A61B 17/1767 |
| 2017/0348012 | A1 * | 12/2017 | Harris | A61F 2/461 |

* cited by examiner

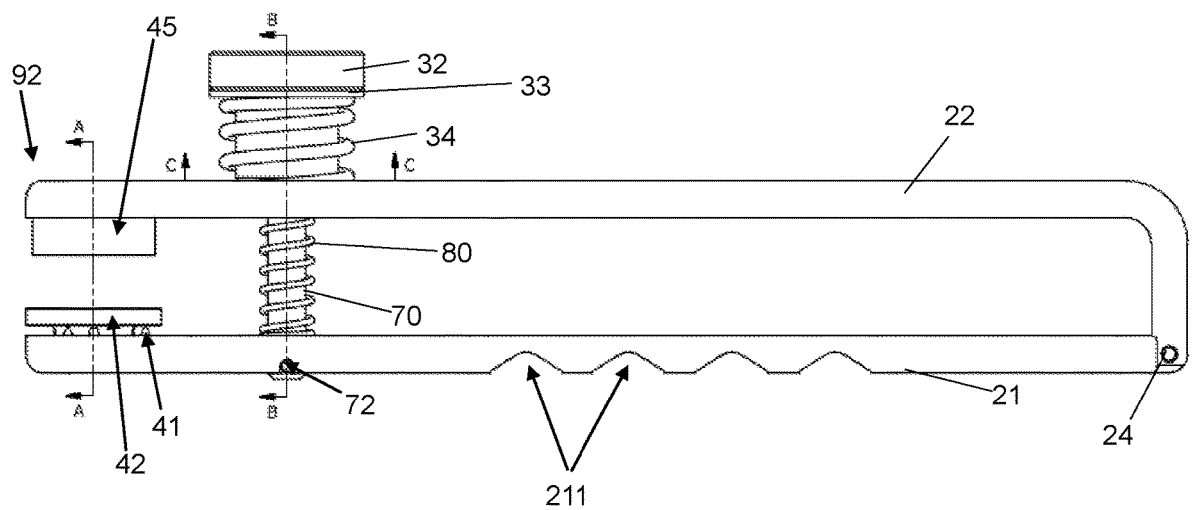
FIG. 3
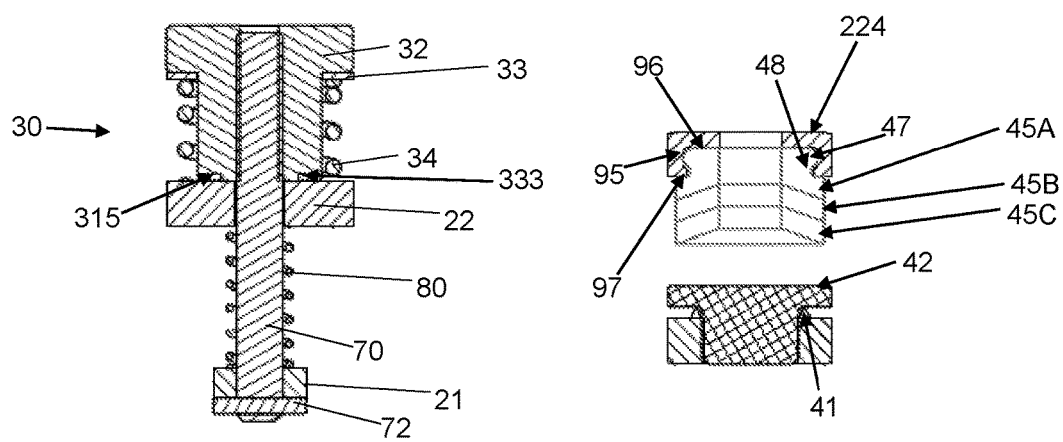
FIG. 5
FIG. 4

ARTIFICIAL PROSTHESIS INSTALLATION CLAMP AND METHOD

CROSS-REFERENCE TO RELATED APPLICATIONS

The present application claims the benefit of, and is a continuation application of, U.S. application Ser. No. 15/798,472, filed on Oct. 31, 2017 and entitled "Artificial Prosthesis Installation Clamp and Method".

TECHNICAL FIELD

The present disclosure relates to medical instrumentation, and more particularly to a device for clamping articles such as artificial prostheses.

BACKGROUND ART

The typical known art of surgically resurfacing the natural patella, when necessary to accept an artificial patella prosthesis, requires the patella to be everted and held in a position allowing the surgeon to have access to the articulating surface which normally articulates within the intercondylar notch between the femoral condyles.

Past efforts to apply consistent, measured pressure to the patella construct are described, for example, in U.S. Pat. Nos. 9,131,974, 9,402,746 and 9,603,721, the disclosures of which are hereby incorporated by reference herein in their entireties. However, past patella clamps have not addressed the need for a clamp and assembly/disassembly method that facilitates quick connection and disconnection for cleaning and re-use while providing consistent and measured pressure to an article being clamped.

DISCLOSURE OF INVENTIVE ASPECTS

In various aspects, embodiments of the device and method as presently disclosed enable the medical professional (e.g., a surgeon) to accurately apply positive linear directional control and known pressure upon an article such as a patella construct throughout the process to the cure state of the bone cement, while providing a re-usable component facilitating post-operative cleaning, quick disconnection and connection.

Aspects and embodiments of the current inventive device receive an article such as an everted patella in its prepared form, whereupon the anterior portion of the natural patella is placed upon a spiked platform of a bottom arm associated with the various embodiments of the device. When a bushing insert or adapter device of the present disclosure contacts the artificial patella of the patella construct, the medical professional can apply controlled pressure, which can optionally be measured through a torque knob that provides a tactile knowledge and reference as to the precise amount of measured applied pressure being applied. As part of controlling applied pressure, the medical professional can squeeze the device together to release an initial lock on the device and positively or negatively rotate the torque knob to obtain the desired pressure.

The bushing adapter device secured to the clamp can then be discarded and the clamp device quickly disassembled and thoroughly cleaned, particularly around areas close to the operative procedure so as to be appropriately processed for further use.

Among other things, embodiments of the device and method of the present disclosure substantially improve procedures in the installation of an artificial patella prosthetic replacement in total knee arthroplasty and is also introductory to additional improvements within a system of surgical instrumentation.

BRIEF DESCRIPTION OF THE DRAWINGS

FIG. 3 is a front elevational view of the device of FIG. 1.

FIG. 4 is a right cross-sectional view of the end of the device taken along line B-B of FIG. 1.

FIG. 5 is a right cross-sectional view of the elements of the device taken along line A-A of FIG. 1.

DETAILED DESCRIPTION OF EMBODIMENTS

Figure 1:
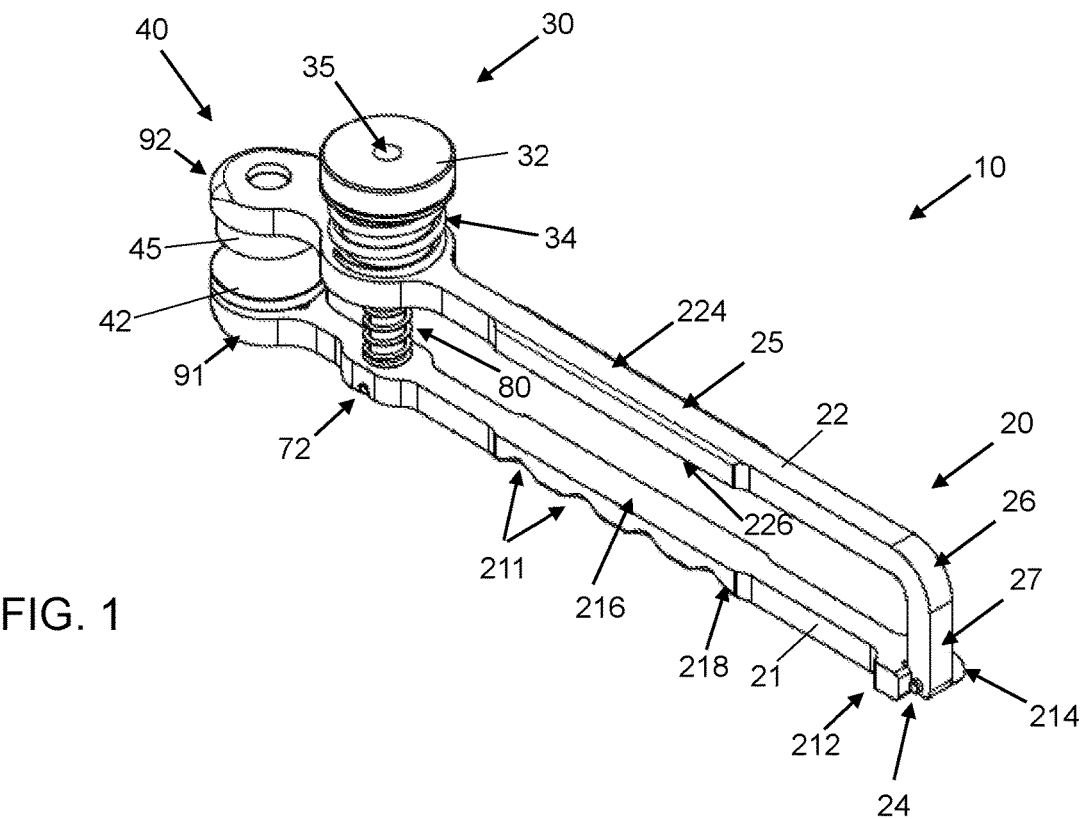
FIG. 1 is a perspective view of an assembled version of one embodiment of a clamp device of the present disclosure.
Figure 2:
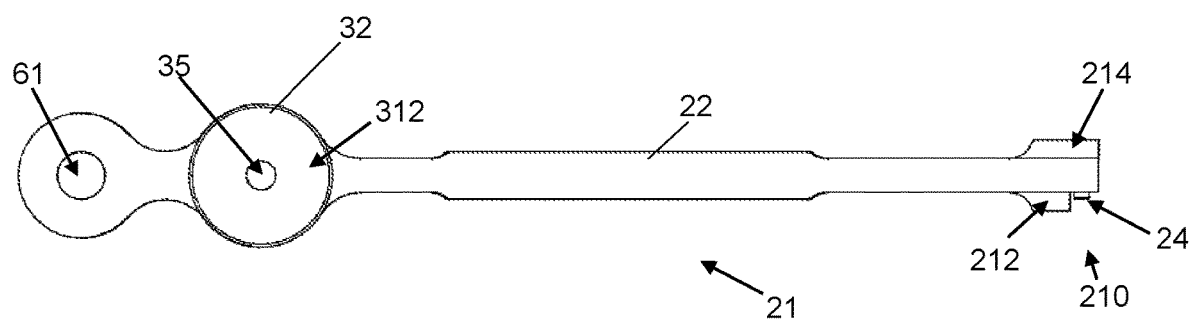
FIG. 2 is a top plan view of the device of FIG. 1.

FIG. 1 is a perspective view of one embodiment of an adjustable measured applied pressure clamp device 10 according to the present disclosure. As shown in FIGS. 1 through 3 and 6, the device 10 comprises a frame assembly 20 for receiving and maintaining a knob assembly 30 and a clamping surface assembly 40.

Figure 6:
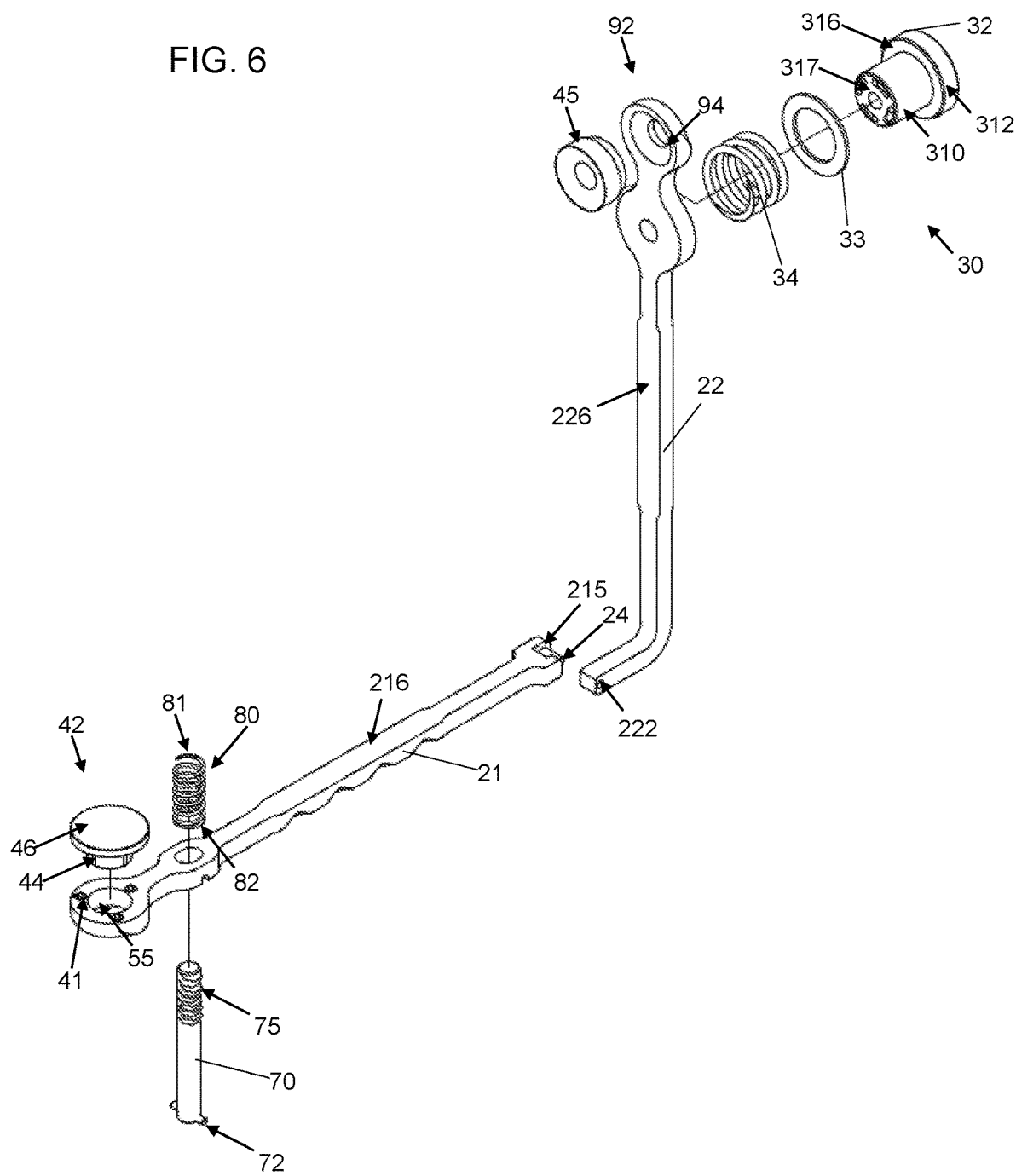
FIG. 6 is an exploded perspective view of the device of FIG. 1, in unassembled form.
Figure 7:
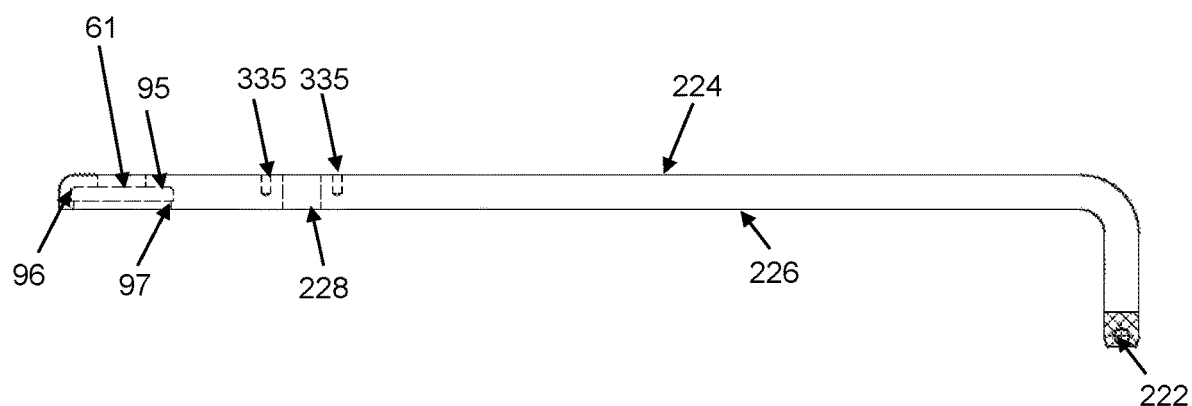
FIG. 7 is a front elevational view of one embodiment of an upper arm of a clamp device according to the present disclosure.
Figure 8:
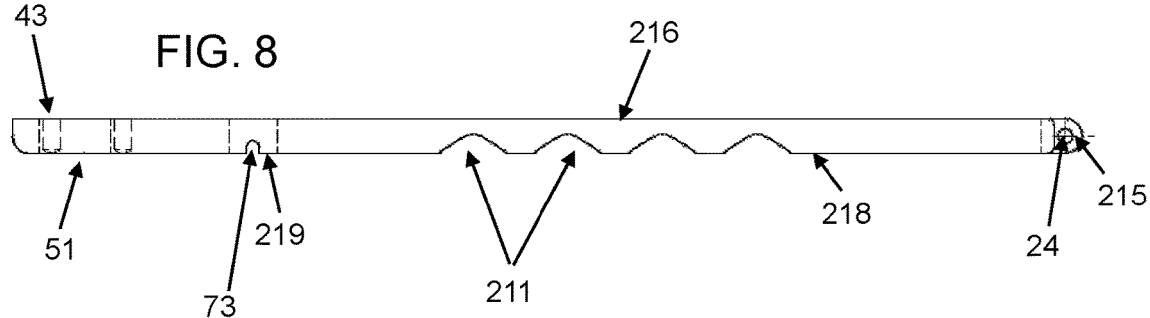
FIG. 8 is a front elevational view of one embodiment of a lower arm of a clamp device according to the present disclosure.

The frame assembly 20 can comprise a bottom arm 21 and a top arm 22, both of which can be made of stainless steel, for example, and are hingedly secured together by, for example, a hinge pin 24. As shown in FIG. 1, the top arm 22 can be formed as a single-piece, unitary, monolithic element having an elongated retention segment 25, a curved joint segment 26 and a bridge segment 27. The bridge segment 27 is generally perpendicular to the elongated retention segment 25. The bottom arm 21 extends generally linearly, and includes a base segment 210 having a first wing extension 212 and a second wing extension 214, both of which extend laterally outwardly from the base segment 210. In various embodiments, the second wing extension 214 also extends linearly beyond the base segment 210. The hinge pin 24 is shown in FIGS. 1, 2, 6 and 8 as extending transverse to the linear extension direction of the bottom arm 21, from the inner surface 215 of the second wing extension 214. In various embodiments, the hinge pin 24 is integrally formed with the second wing extension 214 as part of the monolithic bottom arm 21. Alternatively, the hinge pin 24 can be a separate pin that is inserted into an opening in the inner surface 215 of the second wing extension 214. Regardless of form and attachment means, the hinge pin 24 is insertable through a lateral opening 222 extending through the bridge segment 27 of the top arm 22. In this way, the top arm 22 is hingedly secured to the bottom arm 21, and can rotate in direction C-C (FIG. 3) to a substantially 90-degree relation to the bottom arm 21, as shown in FIG. 6.

As further shown in FIGS. 1 through 3 and 6 through 8, the top arm 22 includes a top surface 224 and a bottom surface 226, and is formed with a spring rod retaining bore 228 extending through the top 224 and bottom 226 surfaces. Similarly, the bottom arm 21 includes an interior surface 216 and an exterior surface 218, and is formed with a spring rod retaining cavity 219 extending through the interior 216 and exterior 218 surfaces. The exterior surface 218 can optionally include indentations 211 to facilitate effective hand gripping during operation of the device. The bore 228 and cavity 219 facility receiving a rod 70 which maintains an internal spring 80 in position such that a top end 81 of the internal spring 80 engages the bottom surface 226 of the top arm 22, and the bottom end 82 of the internal spring 80 engages the interior surface 216 of the bottom arm 21. In this way, as the top 22 and bottom 21 arms are moved towards one another, the internal spring 80 becomes compressed. In various embodiments, the rod 70 is maintained within the bore 228 and cavity 219 via a dowel 72 extending into a dowel-receiving cavity 73 formed in the exterior surface 218 of the bottom arm 21, and also by engaging the torque knob 32 of the knob assembly 30 as described elsewhere herein. The dowel 72 may extend through an opening in the rod 70, or may be integrally formed with the rod 70 as a monolithic structure. The rod 70 is shown as a substantially cylindrical component and includes a threaded or partially threaded exterior surface 75 for engaging the torque knob 32. In various embodiments, the rod 70 is formed of stainless steel.

A clamping surface assembly 40 is secured to the bottom 21 and top 22 arms proximate the respective ends 91 and 92 of the bottom 21 and top 22 arms that are opposite the hinged connection of the arms 21, 22. The assembly 40 can include one or more spikes 41 extending upward from the interior surface 216 of the bottom arm 21. The spikes 41 assist with holding an object being compressed during operation of the device associated with embodiments of the present disclosure. In various embodiments, openings (as at 43 in FIG. 8, for example) can be provided in the bottom arm 21 to receive the spikes 41.

As shown in 1, 3, 5 and 6, an installation cap 42 is provided for assistance with proper setup and operation. The cap 42 can be provided with a substantially cylindrical trunk 44 and lid 46 segments. The cap 42 can be installed in an opening 51 of the bottom arm 21 such that the cylindrical trunk 44 engages the side wall 55 of the bottom arm 21 forming the opening 51, and the lid 46 covers the spike elements 41, such that a user that seeks to employ the device before a procedure is to take place will be protected from minor abrasion. When the device is ready to be used, a user can simply put his or her finger through the opening 51 and push the cap 42 out. Alternatively, cap 42 can be a disc-shaped cap without a trunk, where the cap 42 is placed on top of the spikes 41, with optional indentations for receiving the spikes 41.

The clamping surface assembly 40 further includes a bushing insert 45 maintained within a recessed cavity 94 in the end 92 of the top arm 22. The recessed cavity 94 can be provided by a side wall 95 and upper wall 96 formed into the bottom surface 226 of the top arm 22, wherein the side wall 95 has a lip 97 that has a smaller diameter than the side wall 95 so as to retain a head segment 47 of the bushing insert 45. The head segment 47 extends to a neck segment 48 of smaller diameter than the head segment 47 for secure retention within the cavity 94.

FIG. 5 illustrates that multiple different sizes of bushing inserts 45A, 45B and 45C can be employed depending upon the best fit for a given procedure. While elements 45A, 45B and 45C can be formed so as to engage one another in a nested arrangement, it will be appreciated that different bushing inserts of different dimensions can be provided so as to adapt for smaller, medium-sized and larger patella constructs during operation of the device. Accordingly, in various embodiments, bushing insert 45 of FIG. 3 can be used for patella thicknesses that range from approximately 25.5 mm to 30 mm in a larger embodiment, patella thicknesses that range from approximately 21 mm to 25 mm in a medium embodiment, and patella thicknesses that range from approximately 15 mm to 20.5 mm in a smaller embodiment, so as to provide clamping ability with accurate alignment as described herein.

In various embodiments, each bushing insert 45 can be made of rubber and can be provided for a single use. For example, the top arm 22 includes a throughbore 61 extending through the top 224 and bottom 226 surfaces, which permits a user to simply push out a bushing insert 45 by hand once it has been used. In this way, proper cleaning and sterilization of the device 10 is facilitated for each surgery, with the chances of cross-contamination between surgeries being minimized. In various embodiments, the same three thickness bushing inserts can also be molded on the implant side to match the exact shape of different manufactures of anatomical patella implants. When an anatomical implant is used, a tab or specific feature is molded onto or in the bushing insert allowing exact radial alignment between the anatomical rubber insert and anatomical implant.

It will be appreciated that the bushing inserts can be attached in various ways, such as described, for example, in U.S. Pat. No. 9,603,721, the disclosure of which is incorporated by reference herein in its entirety.

Figure 9:
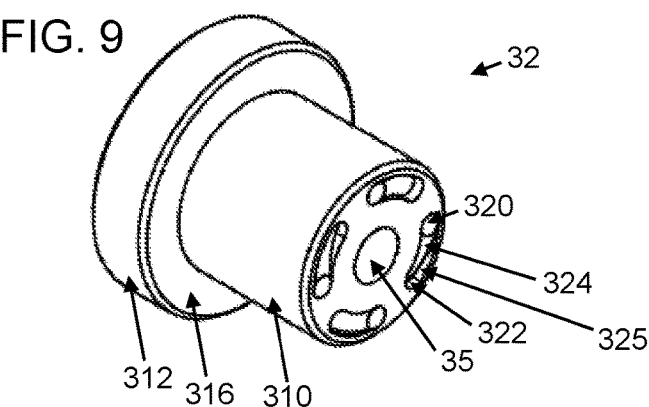
FIG. 9 is a perspective view of one embodiment of a torque knob of a clamp device according to the present disclosure.
Figure 11:
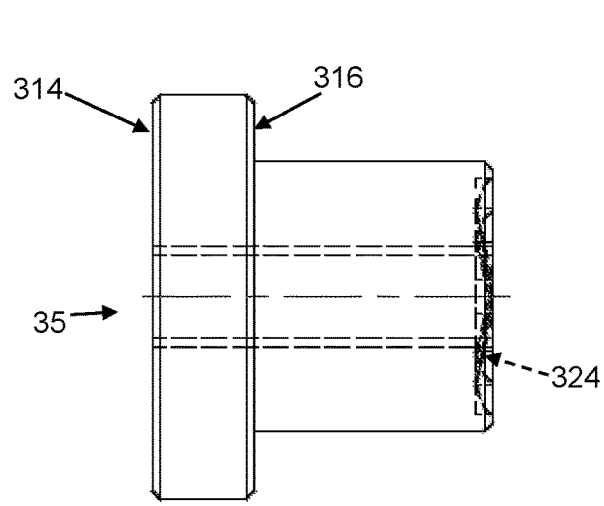
FIG. 11 is a front cross-sectional view taken along line D-D of FIG. 10.
Figure 10:
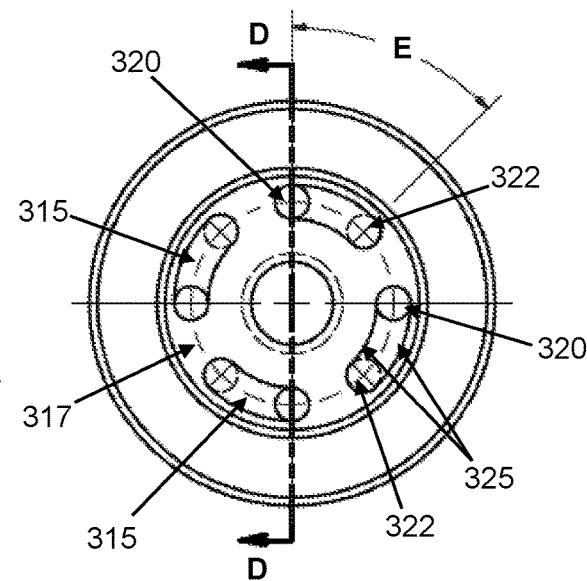
FIG. 10 is a right side view of the torque knob of FIG. 9.

As shown in FIGS. 1 through 4, 6 and 9 through 11, embodiments of the knob assembly 30 in accordance with the present disclosure include a torque knob 32, a thrust bearing 33 and a knob spring 34, which can be called an external spring as it is positioned outside of the top arm 22. As shown in FIGS. 9 through 11, the torque knob 32 includes a substantially cylindrical body 310 integrally formed with a substantially cylindrical head segment 312 so as to form a monolithic structure. In various embodiments, the torque knob 32, internal spring 80 and external spring 34 are formed of stainless steel. A bored opening 35 is formed through the center of the body 310 and head segment 312, and this opening 35 is provided with a thread for threadedly engaging the spring rod 70 during operation. The head segment 312 includes a top surface 314 and an underside surface 316, and the body 310 includes a bottom surface 317 engageable with the top surface 224 of the top arm 22 during operation. The bottom surface 317 is formed with one or more arcuate grooves 315 extending into the torque knob body 310, and in various embodiments, each arcuate groove 315 is formed so as to increase in depth from a first depth 320 adjacent the body bottom surface 317 to a second depth 322 that is greater than the first depth. The increase in depth can progress gradually along a slot 324 with side walls 325 that facilitate a smooth transition for one or more dowel pins 333 maintained in the top surface 224 of the top arm 22. During operation, the torque knob 32 is threadedly connected to the threaded end 75 of the spring rod 70. As the torque knob 32 is tightened to the spring rod 70, the pressure applied to an object held between the bushing insert 45 on the top arm 22 and the spikes 41 on the bottom arm 21 increases. In various embodiments, the pressure can be measured by an auxiliary instrument, such as a strain gauge (not shown) or by the torque knob 32 itself. For instance, the length of the torque knob body 310 and the distance between the bushing insert 45 and spikes 41 when in contact with the object to be desired can be measured and determined to be at a proper distance for applying a desired pressure, such as forty-two pounds per square inch in particular applications. The pressure can be sustained at a certain desired level based on the torque knob 32 being held in place via the dowel pin 333 retention in the deepest part of the arcuate groove 315 of the bottom surface 317 of the torque knob body 310.

In various embodiments, when the torque knob 32 is initially threaded to the spring rod 70, the bottom surface 317 of the body 310 is positioned above the top surface 224 of the top arm 22 with a gap therebetween. Once the torque knob 32 is tightened to the spring rod 70, each dowel pin protruding from the top surface 224 of the top arm 22 extends into a respective one of the slots 324 and/or one of the depth positions 320, 322. As the dowel pin 333 extends from a first position (e.g., 320) in the slot 324 where the slot is shallow to a second position (e.g., 322) in the slot 324 at the point where the slot depth is greatest, a positive stop is created such that the torque knob 32 will not be able to rotate further in a tightening fashion. Nevertheless, the torque knob 32 can be rotated backwards so as to lessen the applied pressure and ultimately disconnect the torque knob 34 from the spring rod 70. If further tightening is required, the arms 21, 22 can be manually squeezed so as to lift the torque knob 32 off of the dowel pins 333, after which the torque knob 32 can be rotated further in a tightening fashion and the manual squeezing of the arms can be stopped, whereby the torque knob slots 324 then engage a different one of the respective dowel pins 333 such that the pressure applied to the article between the bushing insert 45 and spikes is thereby increased. This process can be repeated until the desired pressure is obtained.

As shown in FIG. 10, the bottom surface 317 of the body 310 can be provided with four separate slots 324 of varied depth. Each of these slots 324 correspond to a respective dowel pin 333. In various embodiments, the angle E from a first depth position 320 to a second depth position 322 for a given slot is from approximately 45 degrees to approximately 60 degrees.

In various embodiments, the dowel pins 333 are secured within respective dowel retention chambers 335 formed within the top surface 224 of the top arm 22. The thrust bearing 33 acts as a type of washer providing a uniform contact surface for engaging the underside surface 316 of the head segment 312 and the external spring 34. During operation, through a clockwise rotation of the head segment 312, the dowel pins 333 follow a respective slot 324 downward from a shallower depth to a deeper depth within the respective slot 324. In the embodiments of the present disclosure with one or more springs 34 and/or 70, the spring(s) compress as the torque knob 32 is tightened. The deeper slot retention of the dowel pin 33 combined with the threaded connection of the rod 70 with the bore opening 35 in the torque knob 32 provides a secure, staged compression, which thereby provides for measurable applied and stable pressure upon a patella construct or other object during operation. It will be appreciated that the length of the torque knob body 310 and the distance between the bushing insert 45 and spikes 41 when in contact with the desired object can be pre-established, such that when the arcuate grooves 315 of the torque knob 32 first engage a respective dowel pin 333 while the torque knob body 310 is engaged with the top surface 224 of the top arm, the desired pressure on the object is achieved. Such a desired pressure may be forty-two pounds per square inch in particular applications, for example.

It will be appreciated that the present disclosure can provide different forms of gauging pressure, including a light-emitting diode (LED) or other visual indicator, an auditory indicator, or other form of indicator on the device 10. In various embodiments, the spring 80 and/or the spring 34 is/are required to be compressed to a specific measurable height in order to produce a certain amount (e.g., 42 psi) of desired pressure. In various alternative embodiments, the spring 80 and/or spring 34 is/are provided of appropriate material (e.g., stainless steel), thickness and dimension to provide desired properties such as the desired tensile strength in order for the first engagement of the dowel pins 333 with the deepest ends of respective arcuate grooves 315 of the torque knob 32 to provide the desired amount of pressure to the article being compressed.

It will be appreciated that the assembly embodiments described herein can be adapted to implement and measure a pulling force, to the extent a pulling force is desired on a given article instead of a clamping force.

In exemplary embodiments, one can assume that a body part, such as the patella of a human knee, is being replaced or repaired. With the various embodiments described herein, measured pressure can be applied and accurate positioning accommodated in restoration of the patella, for example.

In a specific embodiment of a method of assembly, the top arm 22 is provided with the spring rod retaining bore 228 formed therethrough, and the bottom arm 21 is provided with the spring rod retaining cavity 219 extending therethrough. The top 22 and bottom 21 arms are hingedly secured as described above. The torque knob 32 is provided with a central opening 35 extending at least through the torque knob body segment 310 and optionally through the torque knob head segment 312. The external spring 34 is also positioned around the body segment 310 of the torque knob 32. The spring rod 70 is inserted into the spring rod retaining cavity 219 of the bottom arm 21, and as it extends through the cavity 219, the internal spring 80 is positioned around the spring rod 70 between the top 22 and bottom 21 arms. Next, the spring rod 70 is inserted through the spring rod retaining bore 228 of the top arm 22 and into the opening 35 of the torque knob 32. As the spring rod 70 and torque knob 32 engage each other, such as through threaded engagement, the bottom surface 317 of the torque knob body segment 310 engages the top surface 224 of the top arm 22, and the bottom end of the external spring 34 also engages the top surface 224 of the top arm 22. Further, the dowel 72 secured to the bottom of the spring rod 70 is pulled into the slot 73 in the bottom arm 21. In this way, the device is quickly assembled, and allows rotation of the torque knob 32 to compress the springs 34, 80 in applying constant, measured pressure to an article to be held between the spikes 41 and the bushing insert 45. It will be appreciated that the device can apply measured pressure without spring 34 or spring 80, or with just one of spring 34 or spring 80, as described above.

The device can be disassembled by reverse rotation of the torque knob 32, which may or may not require manual squeezing of the arms 21, 22 to facilitate rotation. As such, the present disclosure provides for single rod disassembly. Alternatively, in embodiments of the device where the dowel 72 is a separate member retained within a cavity in the spring rod 70, the device can be quickly disassembled by removing the dowel 72, which causes the spring rod 70 and connected torque knob 32 to be releasable through the top 22 and bottom 21 arms. The springs 34 and 80 can then be removed from the torque knob 32 and/or spring rod 70, the spring rod 70 can be unscrewed from the torque knob 32 and the top arm 22 can be de-hinged from the bottom arm 21. Further, the bushing insert 45 can be pushed out of the top arm 22. In this way, the device can be easily assembled and disassembled before/after use, which facilitates thorough and quick cleaning of each element of the device.

During use, an article to be compressed, such as an artificial patella construct, is placed between the spikes 41 and the bushing insert 45. The artificial patella construct generally comprises an artificial patella prosthesis, followed by a bonding agent, followed by a natural patella that has been re-surfaced for facilitating best results in the knee replacement operation. The anterior natural patella is positioned atop the spikes 41. Then, the bonding agent, such as bone cement, is applied, and the natural resurfaced patella is then placed atop the bonding agent. Appropriate pressure must then be applied to properly secure the artificial patella prosthesis with the natural patella.

As the top arm 22 is lowered such that the bushing insert 45 comes in contact with the top of the article being compressed, the torque knob 32 is rotated (typically clockwise) so that the dowel members 333 engage different arcuate grooves 315 as described above, until the desired amount of pressure is being provided to the article. The ratcheting nature of the torque knob 34 against the top arm 22, combined with the threaded connection of the torque knob 34 with the spring rod 70 combines to hold the clamp in a desired position at the desired pressure for the desired length of time.

It will be appreciated that embodiments of the device of the present disclosure establishes the proper amount of measured applied pressure upon the patella construct on all involved and necessary surfaces. So after the initial establishment of pressure, all surfaces settle in the bone cement. To the extent the elements being compressed cause the pressure to change after initially being set, the pressure can be re-established.

It will be appreciated that various embodiments of the present disclosure can employ various material types, including but not restricted to stainless steel, aluminum, brass, plastics and high strength composites, for example. In specific embodiments, the arms 21, 22, the torque knob 32, the spring rod 70 and the spikes 41 are provided in plastic. In additional embodiments, the springs 34, 80 and the thrust bearing 33 are also provided in plastic.

The disclosed device and method may be embodied in other specific forms without departing from the spirit or essential characteristics thereof. The present embodiments are therefore to be considered in all respects as illustrative and not restrictive, the scope being indicated by the claims of the application rather than by the foregoing description, and all changes which come within the meaning and range of equivalency of the claims are therefore intended to be embraced therein.

The invention claimed is:

1. A clamp, comprising:
 a top handle comprising a top surface formed with at least one dowel retention chamber;
 a bottom handle hingedly secured to the top handle;
 a spring rod secured to the bottom handle and engageable with the top handle;
 a torque knob rotatably secured to the spring rod, wherein the torque knob comprises a head segment and a body segment monolithically formed, wherein the body segment comprises a body segment bottom surface engageable with the top surface of the top handle, wherein the torque knob body segment bottom surface is formed with at least one arcuate groove extending into the torque knob body segment; and
 at least one dowel secured within the at least one dowel retention chamber and within the at least one arcuate groove of the torque knob body segment body surface.

2. The clamp of claim 1, wherein the top handle comprises a spring rod retaining bore extending therethrough, and wherein the spring rod is engageable with the top handle by extending through the spring rod retaining bore.

3. The clamp of claim 1, wherein the torque knob is rotatably secured to the spring rod via a threaded connection.

4. The clamp of claim 1, wherein the at least one arcuate groove is formed so as to increase in depth from a first depth adjacent the body segment bottom surface to a second depth that is greater than the first depth.

5. The clamp of claim 4, wherein the torque knob body segment is rotatable from a first position wherein the at least one dowel is secured within the at least one arcuate groove at the first depth to a second position wherein the at least one dowel is secured within the at least one arcuate groove at the second depth.

6. The clamp of claim 1, further comprising an internal spring secured around the spring rod, wherein the internal spring comprises a first end engageable with the bottom surface of the top handle and a second end engageable with the interior surface of the bottom handle.

7. A method for applying substantially constant pressure to a patella construct, comprising:
 applying a clamp to a patella construct, wherein the clamp comprises
  a top handle comprising a top surface formed with at least one dowel retention chamber;
  a bottom handle hingedly secured to the top handle;
  a spring rod secured to the bottom handle and engageable with the top handle;
  a torque knob rotatably secured to the spring rod, wherein the torque knob comprises a head segment and a body segment monolithically formed, wherein the body segment comprises a body segment bottom surface engageable with the top surface of the top handle, wherein the torque knob body segment bottom surface is formed with at least one arcuate groove extending into the torque knob body segment; and
  at least one dowel secured within the at least one dowel retention chamber and within the at least one arcuate groove of the torque knob body segment body surface; and
 locking the clamp in position in order to apply substantially constant pressure to the patella construct.

8. The method of claim 7, wherein the at least one arcuate groove is formed so as to increase in depth from a first depth adjacent the body segment bottom surface to a second depth that is greater than the first depth, and wherein locking the clamp in position comprises rotating the torque knob from a first position wherein the at least one dowel is secured within the at least one arcuate groove at the first depth to a second position wherein the at least one dowel is secured within the at least one arcuate groove at the second depth.

9. The method of claim 7, wherein the top handle comprises a spring rod retaining bore extending therethrough, and wherein the spring rod is engageable with the top handle by extending through the spring rod retaining bore.

10. The method of claim 7, wherein the torque knob is rotatably secured to the spring rod via a threaded connection.

* * * * *